United States Patent
Baxter et al.

(10) Patent No.: US 6,503,910 B1
(45) Date of Patent: Jan. 7, 2003

(54) HYDROXAMIC AND CARBOXYLIC ACID DERIVATIVES

(75) Inventors: Andrew Douglas Baxter, Cambridge (GB); David Alan Owen, Cambridge (GB); Robert John Watson, Cambridge (GB); John Gary Montana, Cambridge (GB)

(73) Assignee: Darwin Discovery Ltd. (GB)

( * ) Notice: Subject to any disclaimer, the term of this patent is extended or adjusted under 35 U.S.C. 154(b) by 0 days.

(21) Appl. No.: 09/622,134

(22) PCT Filed: May 12, 2000

(86) PCT No.: PCT/GB00/01823
§ 371 (c)(1),
(2), (4) Date: Aug. 11, 2000

(87) PCT Pub. No.: WO00/69839
PCT Pub. Date: Nov. 23, 2000

(30) Foreign Application Priority Data

May 12, 1999 (GB) ................................................ 9911073

(51) Int. Cl.[7] .................... A61K 31/495; C07D 241/04; C07D 403/00

(52) U.S. Cl. ............................. 514/252.12; 514/252.13; 514/255.01; 514/255.02; 544/358; 544/359; 544/383; 544/392; 544/402

(58) Field of Search .................................. 544/358, 359, 544/383, 392, 402; 514/252.12, 252.13, 255.02, 255.01

(56) References Cited

FOREIGN PATENT DOCUMENTS

| WO | 9805635 | * | 2/1998 |
| WO | 9816503 | | 4/1998 |

* cited by examiner

*Primary Examiner*—Mukund J. Shah
*Assistant Examiner*—Sudhaker B. Patel
(74) *Attorney, Agent, or Firm*—Saliwanchik, Lloyd & Saliwanchik

(57) ABSTRACT

Compounds of the formula $$(B)_2N-X-(CH_2)_n-CR^1R^2-CO-Y \qquad (I)$$

have therapeutic utility as inhibitors of metalloproteinases etc.

10 Claims, No Drawings

HYDROXAMIC AND CARBOXYLIC ACID DERIVATIVES

FIELD OF THE INVENTION

This invention relates to hydroxamic and carboxylic acid derivatives, and to their use in medicine.

BACKGROUND OF THE INVENTION

Metalloproteinases, including matrix metalloproteinase (MMP), (human fibroblast) collagenase, gelatinase and TNFα convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the ADAM or ADAM-TS families. Members of the ADAM family include TNFα convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNFα both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNFα are described in WO-A-9513289, WO-A-9611209, WO-A-96035687, WO-A-96035711, WO-A-96035712 and WO-A-96035714.

SUMMARY OF THE INVENTION

The invention encompasses novel compounds of formula (I) which are useful inhibitors of matrix metalloproteinases, ADAM or ADAM-TS enzymes, and which are useful for the treatment of diseases indicated by those enzymes and also and/or TNFα-mediated diseases, including degenerative diseases and certain cancers.

Novel compounds according to the invention are of the general type represented by formula (I):

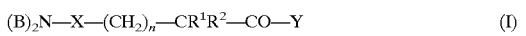

(B)$_2$N—X—(CH$_2$)$_n$—CR$^1$R$^2$—CO—Y   (I)

wherein
  n=0–2;
  X is S(O)$_{1-2}$;
  Y is OH or NHOH;
  CR$^1$R$^2$ is a cycloalkyl, cycloalkenyl, heterocycloalkyl or heterocycloalkenyl ring substituted with a group selected from =O, =CR$^3$R$^4$ and =NOR$^3$, or CR$^1$R$^2$ is a spirocyclic system, optionally substituted with R$^3$ or R$^5$;
  R$^3$ is H or a group (optionally substituted with R$^5$) selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl and C$_{1-6}$ alkyl-heterocycloalkyl;
  R$^4$ is H or C$_{1-6}$ alkyl;
  R$^5$ is OR$^9$, OCF$_3$, OCH$_2$F, OCHF$_2$, COR$^9$, CO$_2$R$^4$, CON(R$^9$)$_2$, N(R$^9$)$_2$, NR$^9$COR$^5$, NR$^9$CON(R$^9$)$_2$, NR$^9$CO$_2$R$^{10}$, NR$^9$SO$_2$R$^{10}$, S(O)$_{0-2}$R$^{10}$, SO$_2$N(R$^9$)$_2$ or cycloimidyl (optionally substituted with R$^6$);
  R$^6$ is C$_{1-6}$ alkyl;
  B is H or a group (optionally substituted with R$^7$) selected from C$_{1-6}$ alkyl, C$_{2-6}$ alkenyl, C$_{2-6}$ alkynyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl, C$_{1-6}$ alkyl-heterocycloalkyl, cycloalkenyl, and heterocycloalkenyl; and each instance of B may be the same or different, provided that NB$_2$ is not NH$_2$;
  or B—N—B is a heterocycloalkyl or heterocycloalkenyl ring optionally substituted with a group selected from R$^7$, =CR$^7$R$^4$, =O and =NOR$^7$, or a spirocyclic system optionally substituted with R$^7$;
  R$^7$ is H, R$^8$ or a group (optionally substituted with R$^8$) selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl and C$_{1-6}$ alkyl-heterocycloalkyl;
  R$^8$ is H or a group selected from N(R$^9$)$_2$, NR$^9$COR$^9$, NR$^9$CON(R$^9$)$_2$, NR$^9$CO$_2$R$^{10}$, NR$^9$SO$_2$R$^{10}$, OR$^9$, OCF$_3$, OCH$_2$F, OCHF$_2$, COR$^9$, CO$_2$R$^4$, CON(R$^9$)$_2$, S(O)$_{0-2}$R$^{10}$ and SO$_2$N(R$^9$)$_2$;
  R$^9$ is H or a group selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl and C$_{1-6}$ alkyl-heterocycloalkyl, wherein said group is optionally substituted with R$^{10}$, COR$^{10}$, SO$_{0-2}$R$^{10}$, CO$_2$R$^{10}$, OR$^{10}$, OCF$_3$, OCH$_2$F, OCHF$_2$, CONR$^4$R$^{10}$, NR$^4$R$^{10}$ or SO$_2$NR$^4$R$^{10}$, and for each case of N(R$^9$)$_2$ the R$^9$ groups are the same or different, or N(R$^9$)$_2$ is heterocycloalkyl optionally substituted with R$^{10}$, COR$^{10}$, SO$_{0-2}$R$^{10}$, CO$_2$R$^{10}$, OR$^{10}$, CONR$^4$R$^{10}$, NR$^4$R$^{10}$, or SO$_2$NR$^4$R$^{10}$; and
  R$^{10}$ is C$_{1-6}$ alkyl, aryl, C$_{1-6}$ alkyl-aryl, heteroaryl or C$_{1-6}$ alkyl-heteroaryl; and the salts, solvates, hydrates, N-oxides, protected amino, protected carboxy and protected hydroxamic acid derivatives thereof.

DESCRIPTION OF THE INVENTION

Preferred compounds of the invention are those wherein any one or more of the following apply: X is SO$_2$; Y is NHOH; B—N—B is optionally substituted heterocycloalkyl; n=1; and CR$^1$R$^2$ is the said cycloalkyl or heterocycloalkyl ring.

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime and/or an alkene. These groups can give rise to geometrical isomers, and in each case the invention is to be understood to extend to all such isomers and mixtures thereof.

As used in this specification, alone or in combination, the term "C$_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "C$_{1-8}$ alkyl" refers to straight or branched chain alkyl moiety having from one to eight carbon atoms, including for example, methyl, ethyl, propyl, isopropyl, butyl, tert-butyl, pentyl, hexyl, octyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "$C_{2-6}$ alkynyl" refers to a straight or branched chain alkyl moiety having two to six carbon atoms and having in addition one triple bond. This term would include for example, ethynyl, 1-propynyl, 1- and 2-butynyl, 1-methyl-2-butynyl etc.

The term "cycloalkyl" refers to a saturated alicyclic moiety having from three to six carbon atoms and includes for example cyclopropyl cyclobutyl, cyclopentyl, cyclohexyl and the like.

The term "cycloalkenyl" refers to an alicyclic moiety having from three to six carbon atoms and having in addition one double bond. This term includes, for example, cyclopentenyl and cyclohexenyl.

The term "heterocycloalkyl" refers to a saturated heterocyclic moiety having from two to six carbon atoms and one or more heteroatom from the group N, O, S (or oxidised versions thereof) which may be optionally benzofused at any available position. This includes for example azetidinyl, pyrrolidinyl, tetrahydrofuranyl, piperidinyl, benzodioxole and the like.

The term "heterocycloalkenyl" refers to an alicyclic moiety having from three to six carbon atoms and one or more heteroatoms from the group N, O, S and having in addition one double bond. This term includes, for example, dihydropyranyl.

The term "aryl" refers to an aromatic carbocyclic radical having a single ring or two condensed rings, optionally substituted with an aryl group substituent. This term includes, for example phenyl or naphthyl.

The term "heteroaryl" refers to aromatic ring systems of five to ten atoms of which at least one atom is selected from O, N and S, and optionally substituted with an aryl group substituent. This term includes for example furanyl, thiophenyl, pyridyl, indolyl, quinolyl and the like.

The term "spirocyclic system" refers to a bicyclic system of which the two rings have a single common carbon atom and in which each ring is as defined above for cycloalkyl, cycloalkenyl, heterocycloalkyl or heterocycloalkenyl. Thus, each ring has 3 to 6 atoms which may all be C atoms or which may include one or more heteroatoms selected from N, O and S. Any unsaturation may be in either ring. This term includes, for example, spiro[4.5]decanyl.

The term "aryl group substituent" refers to a substituent chosen from halogen, CN, $CF_3$, $CHF_2$, $CH_2F$, and $NO_2$.

The term "halogen" means fluorine, chlorine, bromine or iodine.

The term "benzofused" refers to the addition of a benzene ring sharing a common bond with the defined ring system.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "optionally substituted" means optionally substituted with one or more of the groups specified, at any available position or positions.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamnine salts.

When the "protected carboxy" group in compounds of the invention is an esterified carboxyl group, it may be a metabolically-labile ester of formula $CO_2R^{11}$ where $R^{11}$ may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$; $R^8$, $R^9$, $R^{10}$, $R^{11}$, B, X and Y are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises acylating an amine of formula $B_2NH$ (II) with an acylating agent of formula Z—X—$(CH_2)_n$—$CR^1R^2$—COY (III) wherein Z represents a suitable leaving group (e.g. a halogen such as chlorine), and Y is OH or NHOH or protected forms thereof such as $OR^{12}$ (where $R^{12}$ is a suitable protecting group such as benzyl or tert-butyl) or $NHOR^{13}$ (where $R^{13}$ is benzyl, tert-butyl or tert-butyldimethylsilyl).

Acylating agents of formula (III) where X is $SO_2$ may be prepared from compounds of formula $R^{14}S$—$(CH_2)_n$—$CR^1R^2$—COY (IV), where $R^{14}$ is H or a suitable labile group such as acetyl, by treatment with chlorine in an appropriate solvent such as water at an appropriate temperature such as 0° C. Acylating agents of formula (III) where X=SO may be prepared from compound (VI) by treatment with $SO_2Cl_2$ and acetic anhydride in an appropriate solvent such as dichloromethane at an appropriate temperature such as 0° C.

Sulfanyl compounds of formula (IV) may be prepared readily by alkylation of a compound $R^{12}SH$ with an alkylating agent of the form $Z^A$—$(CH_2)_n$—$CR^1R^2$—COY (V), where $Z^A$ is a leaving group (e.g. a halogen such as bromine, or an alkylsulfonate ester such as methanesulfonate).

Alkylating agents of formula (V), if not available commercially, may be prepared from alcohols of formula HO—$(CH_2)_n$—$CR^1R^2$—COY (VI). For example, when $Z^A$ is a methanesulfonate ester, compound (V) may be prepared from compound (VI) by reaction with methanesulfonylchloride in an inert solvent such as dichloromethane in the presence of an organic base such as diisopropylethamine.

When n=1 and $Z^A$ is Br, compounds of formula (V) and (VI) may also be prepared from compounds of formula $HCR^1R^2COY$ (VII) by reaction with a strong base (such as lithiumdiisopropylamide) and $CH_2CBr_2$ in an inert solvent such as tetrahydrofuran. Similarly when n=1, compounds of formula (VI) may also be prepared from (VII) by reaction with a strong base (such as lithiumdiisopropylamide) and paraformaldehyde in an inert solvent such as tetrahydrofuran.

Many amines of formula (II) are available commercially, or may be prepared from amines available commercially by standard chemical methods known to those skilled in the art.

Compounds of formula (I) may also be prepared by interconversion of other compounds of formula (I). Thus, for example, compound of formula (I) where $X=SO_2$ may be prepared from a compound of formula (I) where X=SO by oxidation with, for example sodium periodate and ruthenium chloride trihydrate in an appropriate solvent, for example acetonitrile-tetrachloromethane-water. Hydroxamic acids (Y=NHOH) of general formula (I) may be prepared from carboxylic acids (Y=OH) of formula (I) using methods known to those skilled in the art.

Compounds of formula (1) in which B or $CR^1R^2$ is substituted by =$CR^3R^4$ or =$CR^7R^4$ respectively may be prepared from the corresponding ketones using any standard procedure, for example by employing a Wittig reaction. Compounds of formula (1) in which B or $CR^1R^2$ is substituted by =$NOR^3$ or =$NOR^7$ respectively may also be prepared from the corresponding ketones by any standard procedures known to those skilled in the art, for example by reacting the ketone with a hydroxylamine of formula $H_2NOR^3$ (VIII) or $H_2NOR^7$ (IX). Hydroxylamines of formula (VIII) and (IX) may be commercially available or may be prepared by standard conditions known to those skilled in the art.

Similarly, intermediates of any appropriate formula may be prepared by the interconversion of other compounds of the same formula. Thus, for example, a compound of formula (VII) where $R^2$ is not H may be prepared from a compound of formula (VI) where $R^2$ is H by reaction with a compound $R^2Z$ (where Z is as defined above) in the presence of a strong base such as lithiumdiisopropylamide in an inert solvent such as tetrahydrofuran.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysin, collagenase, gelatinase, ADAM and ADAM-TS enzymes. Compounds according to the invention may also exhibit in vitro inhibition of membrane shedding events known to be mediated by metalloproteinases, for example, α-APP, ACE, TGF-α, TNF-α, Fas ligand, selecting, TNFR-I, TNFR-II, CD30, Il-6R, CD43, CD44, CD16-I, CD16-II, Folate receptor, CD23, or IL-1RII.

The activity and selectivity of the compounds may be determined by use of the appropriate enzyme inhibition test, for example as described in Examples A–M of WO-A-9805635, by the assay for the inhibition of CD23 shedding described in WO-A-9924399, or by the following assay of TNF RI shedding.

The potency of the compounds of general formula (I) to act as inhibitors of the production of TNF RI is determined using the following procedure. A 100 $\mu$M solution of the inhibitor being tested or dilutions thereof is incubated at 37° C. in an atmosphere of 5% $CO_2$ with peripheral blood mononuclear cells (PBMC). PBMC are isolated from buffy coats by standard procedures using Ficoll. A 100 $\mu$M solution of the inhibitor being tested or dilutions thereof is incubated for 22 hours at 37° C. in an atmosphere of 5% $CO_2$ with 1×10$^8$/ml PBMC stimulated with LPS. The cells are centrifuged down and the supernatant is assayed for TNF RI using a commercially available ELISA kit (R & D Systems). The activity in the presence of 0.1 mM inhibitor or dilutions thereof is compared to activity in a control devoid of inhibitor and results reported as that inhibitor concentration effecting 50% inhibition of the production of TNF RI.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases, cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, bacterial infections, HIV infections, fever, shock states, graft versus host reactions, dermatological conditions, surgical wound healing, psoriasis, atopic dermatitis, epidermolysis buflosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus and solid organ transplant.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. No. 4,256,108, U.S. Pat. No. 4,166,452 and U.S. Pat. No. 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouthwashes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples are of compounds that illustrate the invention, and the Intermediates relate to steps in their preparation.

INTERMEDIATE 1

8-Acetylthiomethyl-1,4-dioxaspiro[4.5]decane-8-carboxylic Acid Ethyl Ester

Potassium thioacetate (1.0 g) was added to a solution of 8-bromomethyl-1,4-dioxa-spiro[4.5]decane-8-carboxylic acid ethyl ester (1.0 g) in DMF (30 ml) and the solution was heated at 80° C. for 4 h. The mixture was then added to water (100 ml) and extracted with ether. The solvent was washed with water, bicarbonate solution and brine, then dried ($MgSO_4$) and evaporated to give the title compound (1.0 g) as colourless oil.

$R_f$ 0.45 (ether).

INTERMEDIATE 2

8-Chlorosulfonylmethyl-1,4-dioxaspiro[4.5]decane-8-carboxylic Acid Ethyl Ester

A solution of Intermediate 1 (1.0 g) and sodium acetate (1.0 g) in DCM (20 ml) and water (20 ml) was treated with chlorine gas at 0° C. for 1 h. The phases were separated and the organic layer was then washed with cold water and brine, dried ($MgSO_4$) and evaporated to give the title compound (0.93 g) as colourless oil.

$R_f$ 0.34 (ether).

INTERMEDIATE 3

8-[4-(4-Chlorophenyl)piperazine-1-sulfonylmethyl]-1,4-dioxaspiro[4.5]decane-8-carboxylic Acid Ethyl Ester 4-Chlorophenylpiperazine dihydrochloride (0.66 g) was suspended in DCM and triethylamine (0.8 g) was added. The mixture was stirred for 30 minutes, then a solution of Intermediate 2 (1.0 g) was added and the solution stirred for 2 h at room temperature. The mixture was washed with dilute aqueous citric acid, aqueous sodium bicarbonate, water and brine, then dried ($MgSO_4$) and evaporated to give the title compound (0.43 g) as beige solid.

$R_f$ 0.40 (ether).

EXAMPLE 1

8-[4-(4-Chlorophenyl)piperazine-1-sulfonylmethyl]-1,4-dioxaspiro[4.5]decane-8-carboxylic Acid A solution of Intermediate 3 (0.40 g) was heated under reflux in a solution of lithium hydroxide (0.40 g) in 40% aqueous methanol (30 ml) for 2 h, then the solution was evaporated to half volume and washed with ether (2×20 ml). The aqueous layer was acidified to pH 5 with citric acid and extracted with ethyl acetate (2×30 ml). The organic solvent was then washed with water and brine, dried ($MgSO_4$) and evaporated to give the title compound (0.20 g) as colourless solid.

$R_f$ 0.32 (EtOAc).

EXAMPLE 2

8-[4-(4-Chlorophenyl)piperazine-1-sulfonylmethyl]-1,4-dioxaspiro[4.5]decane-8-carboxylic Acid N-Hydroxy Amide Oxalyl chloride (0.4 ml) was added to a solution of Example 1 (0.20 g) in DCM (10 ml) and pyridine (0.2 ml) at room temperature. DMF (0.01 ml) was added and the mixture was stirred for 1 h, then evaporated to dryness and azeotroped with DCM/hexanes (2×20 ml). The residue was dissolved in tetrahydrofuran and an aqueous solution of hydroxylamine (40% w/w, 0.5 ml) was added. The mixture was stirred for 4 min, then water (10 ml) was added and the tetrahydrofuran was removed by vacuum distillation. The aqueous mixture was extracted with ethyl acetate and the solvent washed with brine, then dried ($MgSO_4$) and evaporated. The orange residue was purified by flash column chromatography on silica gel, eluting with 8% methanol in dichloromethane, to give the title compound (0.15 g) as colourless solid.

$R_f$ 0.40 (10% $MeOH/CH_2Cl_2$).

EXAMPLE 3

1-[4-(4-Chlorophenyl)piperazine-1-sulfonylmethyl]-4-oxo-cyclohexanecarboxylic Acid N-Hydroxy Amide A solution of Example 2 and 4-toluenesulfonic acid (0.10 g) in tetrahydrofuran (10 ml) and water (5 ml) was heated under reflux for 4 h, then evaporated to remove the tetrahydrofuran, and the pH was adjusted to 8 with solid sodium bicarbonate. The aqueous residue was extracted with ethyl acetate, and the solvent was washed with water and brine, then dried (MgSO$_4$) and evaporated to give the title compound (0.075 g) as a beige solid.

R$_f$ 0.32 (10% MeOH/CH$_2$Cl$_2$).

MS 429 (M+).

EXAMPLE 4

1-[4-(4-Chlorophenyl)piperazine-1-sulphonylmethyl]-4-methoxyiminocylohexanecarboxylic Acid N-Hydroxy Amide Methoxylamine hydrochloride (20 mg) was added to a solution of Example 3 (12 mg) in ethanol (3 ml) and sodium acetate (10 mg) was added. The mixture was stirred for 3 h, then evaporated in vacuo and water (10 ml) was added. The mixture was extracted with DCM (2×3 ml) and the combined solvent layer washed with water and brine, dried and evaporated to give the title compound as colourless solid (10 mg).

R$_f$ 0.55 (6% MeOH/DCM).

MS 459 (m+1).

What is claimed is:

1. A compound of formula (I)

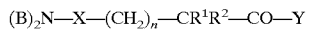   (I)

wherein n=0–2;

X is S(O)$_{1-2}$;

Y is OH or NHOH;

CR$^1$R$^2$ is a cycloalkyl ring substituted with a group selected from =O, =CR$^3$R$^4$ or =NOR$^3$, or CR$^1$R$^2$ is dioxaspirodecane optionally substituted with R$^3$ or R$^5$;

R$^3$ is H or a group (optionally substituted with R$^5$) selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, hetercycloalkyl or C$_{1-6}$ alkyl-heterocycloalkyl;

R$^4$ is H or C$_{1-6}$ alkyl;

R$^5$ is OR$^9$, OCF$_3$, OCH$_2$F, OCHF$_2$, COR$^9$, CO$_2$R$^4$, CON(R$^9$)$_2$, N(R$^9$)$_2$, NR$^9$COR$^9$, NR$^9$CON(R$^9$)$_2$, NR$^9$CO$_2$R$^{10}$, NR$^9$SO$_2$R$^{10}$, S(O)$_{0-2}$R$^{10}$, SO$_2$N(R$^9$)$_2$ or cycloimidyl (optionally substituted with R$^6$);

R$^6$ is C$_{1-6}$ alkyl;

(B)$_2$N is a piperazine optionally substituted with a group selected from R$^7$, =CR$^7$R$^4$, =O or =NOR$^7$;

R$^7$ is H, R$^8$ or a group (optionally substituted with R$^8$) selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl or C$_{1-6}$ alkyl-heterocycloalkyl;

R$^8$ is H or a group selected from N(R$^9$)$_2$, NR$^9$COR$^9$, NR$^9$CON(R$^9$)$_2$, NR$^9$CO$_2$R$^{10}$, NR$^9$SO$_2$R$^{10}$, OR$^9$, OCF$_3$, OCH$_2$F, OCHF$_2$, COR$^9$, CO$_2$R$^4$, CON(R$^9$)$_2$, S(O)$_{0-2}$R$^{10}$ or SO$_2$N(R$^9$)$_2$;

R$^9$ is H or a group selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl or C$_{1-6}$ alkyl-heterocycloalkyl, wherein said group is optionally substituted with R$^{10}$, COR$^{10}$, SO$_{0-2}$R$^{10}$, CO$_2$R$^{10}$, OR$^{10}$, OCF$_3$, OCH$_2$F, OCHF$_2$, CONR$^4$R$^{10}$, NR$^4$R$^{10}$, or SO$_2$NR$^4$R$^{10}$ and for each case of N(R$^9$)$_2$ the R$^9$ groups are the same or different, or N(R$^9$)$_2$ is heterocycloalkyl optionally substituted with R$^{10}$, COR$^{10}$, SO$_{0-2}$R$^{10}$, CO$_2$R$^{10}$OR$^{10}$, CONR$^4$R$^{10}$, NR$^4$R$^{10}$, or SO$_2$NR$^4$R$^{10}$, and R$^{10}$ is C$_{1-6}$ alkyl, aryl, C$_{1-6}$ alkyl-aryl, heteroaryl or C$_{1-6}$ alkyl-heteroaryl;

and the salts, solvates, hydrates, N-oxides, protected amino, protected carboxy and protected hydroxamic acid derivatives thereof.

2. The compound according to claim 1, wherein Y is NHOH.

3. The compound according to claim 1, wherein X is SO$_2$.

4. The compound according to claim 1, wherein n=1.

5. The compound according to claim 1, wherein CR$^1$R$^2$ is said cycloalkyl ring.

6. The compound according to claim 1, wherein none of R$^5$ and R$^9$ is OCF$_3$, OCH$_2$F or OCHF$_2$.

7. The compound according to claim 1, which is

8-[4-(4-chlorophenyl)piperazine-1-sulfonylmethyl]-1,4-dioxaspiro[4.5]decane-8-carboxylic acid 8-[4-(4-chlorophenyl)piperazine-1-sulfonylmethyl]-1,4-dioxaspiro[4.5]decane-8-carboxylic acid N-hydroxyamide or 1-[4-(4-chlorophenyl)piperazine-1-sulfonylmethyl]-4-oxo-cyclohexanecarboxylic acid N-hydroxyamide.

8. The compound according to claim 1, which is 1-[4-(4-chlorophenyl)piperazine-1-sulphonylmethyl]-4-methoxyiminocylohexanecarboxylic acid N-hydroxyamide.

9. The compound according to claim 1, which is chiral and in the form of a single enantiomer or diastereomer.

10. A pharmaceutical composition for use in therapy, comprising a compound of claim 1, and a pharmaceutically-acceptable diluent or carrier.

* * * * *

UNITED STATES PATENT AND TRADEMARK OFFICE
CERTIFICATE OF CORRECTION

PATENT NO.    : 6,503,910 B1
DATED         : January 7, 2003
INVENTOR(S)   : Andrew Douglas Baxter et al.

It is certified that error appears in the above-identified patent and that said Letters Patent is hereby corrected as shown below:

<u>Column 12,</u>
Line 19, "$CO_2R^{10}OR^{10}$" should read -- $CO_2R^{10}$, $OR^{10}$ --.

Signed and Sealed this

Twenty-ninth Day of April, 2003

JAMES E. ROGAN
*Director of the United States Patent and Trademark Office*